US006585759B1

(12) United States Patent
Baum et al.

(10) Patent No.: US 6,585,759 B1
(45) Date of Patent: Jul. 1, 2003

(54) METHOD AND APPARATUS FOR MANUFACTURING MEDICAL SUPPORT DEVICES

(75) Inventors: Abraham Baum, Givataim (IL); Elisha Hoch, Rehovot (IL); Israel Schnitzer, Tel Aviv (IL); Lior Kacir, Rehovot (IL); Felix Rabinovich, Rishon Lezion (IL); Ilia Reuben, Beersheva (IL)

(73) Assignee: Israel Aircraft Industries Ltd. (IL)

( * ) Notice: Subject to any disclaimer, the term of this patent is extended or adjusted under 35 U.S.C. 154(b) by 0 days.

(21) Appl. No.: 09/465,115

(22) Filed: Dec. 16, 1999

(51) Int. Cl.[7] ............................. A61F 2/24; A61F 2/76; A61F 2/06
(52) U.S. Cl. .................... 623/1.18; 623/901
(58) Field of Search ............... 623/901, 1.11, 623/1.12, 1.13, 1.14, 1.15, 1.16, 1.17, 1.18, 1.19, 1.2, 1.21, 1.22; 606/108, 191, 194, 195; 608/198

(56) References Cited

U.S. PATENT DOCUMENTS

| 4,713,049 A | 12/1987 | Carter ........................... 604/8 |
| 4,787,884 A | 11/1988 | Goldberg ....................... 604/8 |
| 4,820,262 A | 4/1989 | Finney .......................... 604/8 |
| 4,874,360 A | 10/1989 | Goldberg et al. ............... 604/8 |
| 5,073,694 A | 12/1991 | Tessier et al. ........... 219/121.7 |
| 5,345,057 A | 9/1994 | Muller .................. 219/121.71 |
| 5,531,741 A | 7/1996 | Barbacci ...................... 606/15 |
| 5,548,894 A | 8/1996 | Muto ........................ 29/890.1 |
| 5,707,385 A | 1/1998 | Williams .................... 606/192 |
| 5,725,548 A | 3/1998 | Jayaraman ................. 606/198 |
| 5,767,480 A | 6/1998 | Anglin et al. .......... 219/121.69 |
| 5,780,807 A | 7/1998 | Saunders ............... 219/121.71 |
| 5,817,126 A | 10/1998 | Imron ........................ 606/198 |
| 5,826,330 A | 10/1998 | Isoda et al. .................. 29/852 |
| 5,843,117 A | 12/1998 | Alt et al. ..................... 606/194 |
| 5,843,161 A | 12/1998 | Solovay ......................... 623/1 |
| 5,843,172 A | 12/1998 | Yan .............................. 623/1 |
| 5,843,175 A | 12/1998 | Frantzen ........................ 623/1 |
| 5,899,917 A | * | 5/1999 | Edwards et al. ............ 606/195 |
| 5,906,759 A | * | 5/1999 | Richter .................. 219/121.63 |

OTHER PUBLICATIONS

V.S. Balanethiram, Xiaoyu Hu, Marina Altynova and Glenn S. Daehn "Hyperplasticity: Enhanced Formability at High Rates" Journal of Materials Processing Technology, vol. 45, 1994, pp. 95–600.

Metals Handbook, 9th Ed. vol. 14, Forming and Forging, ASM Electromagnetic Forming International, Metals Park, OH, pp. 644–653.

G.S. Daehn, M. Altynova, V.s. Balanethiram, G. Fenton, M. Padmanabhan, A. Tamhane, and E. Winnard "High–Velocity Metal Forming—An Old Technology Addresses New Problems", JOM, vol. 7, Jul. 1995, pp. 42–45.

* cited by examiner

Primary Examiner—Kevin T. Truong
Assistant Examiner—Vy Q. Bui
(74) Attorney, Agent, or Firm—Paul J. Sutton

(57) ABSTRACT

Method for producing a medical support device from an object, using an electromagnetic field generator, whereby the method comprises of the steps of placing a formation mandrel against the object, close to a predetermined formation area, and applying the electromagnetic field to the formation area, thereby forming the object. The produced object can be made from a tubular segment, a folded sheet of material or a plurality of wires joined together.

9 Claims, 13 Drawing Sheets

METHOD AND APPARATUS FOR MANUFACTURING MEDICAL SUPPORT DEVICES

FIELD OF THE INVENTION

The present invention relates to a method and apparatus for manufacturing medical devices, in general and to a method and apparatus for manufacturing medical support devices, in particular.

BACKGROUND OF THE INVENTION

Medical support devices are known in the art. An artery support device is also called a stent. Methods for manufacturing stents are known in the art. U.S. Pat. No. 5,767,480, to Anglin et al, is directed to a hole generation and lead forming for integrated circuit lead frames using laser machining.

U.S. Pat. No. 5,073,694 to Tessier et al, is directed to a method and apparatus for laser cutting a hollow metal workpiece. The method provides for the cutting of the hollow metal workpiece while minimizing or eliminating residue adherence to the inner circumference of the workpiece. Coolant is pumped through the apparatus to contact the inner portion of the workpiece before and during laser cutting.

U.S. Pat. No. 5,345,057 to Muller, is directed to a method of cutting an aperture in a device by means of a laser beam.

U.S. Pat. No. 5,780,807 to Saunders, is directed to a method and apparatus for direct laser cutting of metal stents. The expandable stent is made from a single length of tubing and utilizes direct laser cutting from a single metal tube using a finely focused laser beam. The stent may be made in a variety of ways, but the preferred method provides for cutting a thin-walled tubular member of materials such as stainless steel in order to remove portions of the tubing and give a desired pattern. This is done by utilizing a laser beam.

U.S. Pat. No. 5,707,385 to Williams, is directed to a drug loaded elastic membrane comprising an expandable sheath for delivering a therapeutic drug in a body lumen. The expandable membrane has a first layer and a second layer, which are joined along their edges to form a fluid-tight seal. Before joining the layers, a plurality of apertures are formed in the first layer by known methods such as using a laser.

U.S. Pat. No. 5,843,117 to Alt et al, is directed to an implantable vascular and endoluminal stent and the process of fabricating the same. Tube-type stent is fabricated from tubing with longitudinally oriented struts interconnected by bars or bridges, which define a plurality of through-holes in the wall of the tube. This multiplicity of through-holes is cut by a laser beam.

U.S. Pat. No. 5,531,741 to Barbacci, is directed to illuminate stents which are designed as an improved light emitting device. The stent is formed by extruding a length of tubing and then followed by molding and shaping. Drainage openings are formed in one step of the process. These holes may be made by piercing the wall of the tubing by utilizing a sharpened cutter or by use of a laser.

Electromagnetic forming (EMF) is known in the art. In general, this method is used to form, cut, pierce, and join metals having relatively high electrical conductivity, such as copper, mild alloy, aluminum, low-carbon steel, brass, and molybdenum. The EMF process uses a capacitor bank, a forming coil, a field shaper (mandrel), and an electrically conductive workpiece to create intense magnetic fields that are used to do useful work. This intense magnetic field, produced by the discharge of a bank of capacitors into a forming coil, lasts only a few microseconds. The resulting eddy currents that are induced in a conductive workpiece that is placed close to the coil, then interact with the magnetic field to cause mutual repulsion between the workpiece and the forming coil. The force of this repulsion is sufficient to stress the work metal beyond its yield strength, resulting in a permanent deformation. The magnetic field rapidly accelerates the workpiece against the mandrel, thus forming it to the desired shape. Because the actual forming takes place in a matter of a few microseconds, the high strain rate forming does not affect the material properties in an adverse way. The pressure induced on the workpiece, is comparable to that encountered in mechanical forming of similar parts.

EMF can be usually applied to five forming methods: compression, expansion, contour forming, punching and joining. It is used to expand, compress, or form tubular shapes, to form a flat sheet, and to combine several forming and assembly operations into a single step. It is used in single-step assembly of metal parts to each other or to other components, such as in electrical cables, and joining of aluminum and copper. Highly resistant metals such as titanium, need special EMF equipment, which operate at higher frequencies in the range of 20 to 100kHz.

Because the material is loaded into its plastic region, the springback often associated with mechanical forming, is virtually absent in electroformed parts. Joints made by EMF process are typically stronger than the parent material, and compared to other joining methods, such as laser welding. Assemblies using metal parts formed onto plastics, composites, rubber, and ceramics are also common.

More information regarding EMF can be found in the following references: V. S. Balanethiram, Xiaoyu Hu, Marina Altynova and Glenn S. Daehn, "High Velocity forming: Is it Time to Rediscover This Technology", Engineering Research Center Report ERC/NSM-S-94-15, The Ohio State University, Columbus, OH, 1994, PP. 36–37, V. S. Balanethiram, Xiaoyu Hu, Marina Altynova and Glenn S. Daehn, "Hyperplasticity: Enhanced Formability at High Rates", Journal of Materials Processing Technology, Vol. 45, 1994, pp. 595–600, G. S. Daehn, M. Altynova, V. S. Balanethiram, G. Fenton, M. Padmanabhan, A. Tamhane, and E. Winnard, "High-Velocity Metal Forming—An Old Technology Addresses New Problems", JOM, Vol. 7, July 1995, pp. 42–45, and Metals Handbook, $9^{th}$Edition, Volume 14, Forming & Forging, ASM Electromagnetic Forming International, Metals Park, Ohio, pp. 644–653.

SUMMARY OF THE PRESENT INVENTION

It is an object of the present invention to provide a novel method or manufacturing medical support devices, which overcomes the disadvantages of the prior art.

It is an object of the present invention to provide a novel method for manufacturing metal medical devices, while maintaining their original characteristics, which overcomes the disadvantages of the prior art.

In accordance with the present invention, there is thus provided a method for producing a medical support device from at least one object, using an electromagnetic field generator. The method includes the steps of: placing a forming mandrel against the at least one object in the vicinity of a predetermined formation area, and applying at least one electromagnetic field on the formation area, thereby forming the shape of the at least one object.

The method can further include the steps of determining the formation area on the object and repeating from the step of determining, so that additional formation areas define a final shape for the at least one object, the final shape being generally cylindrical.

According to one aspect of the present invention, the object has a tubular shape. In this case, the forming mandrel includes at least one opening, wherein the step of determining includes positioning a selected one of the openings underneath a selected one of the formation areas. Hence, the result of the step of applying an electromagnetic field is punching of material within the selected formation area.

According to another aspect of the invention, the tubular object is made of a material, which can be selected from families of shape memory materials, super elastic materials, stainless steel, alloys, polymeric materials, biocompatible materials, and the like. Accordingly, method can further include a preliminary step of applying shape memory characteristics to the tubular object. Alternatively, the method can also include a final step of applying shape memory characteristics to the tubular object.

In accordance with another preferred embodiment of the present invention, there is thus provided a method for producing a medical support device from a hollow tubular object. The method include the steps of: placing a predetermined mandrel against each of a plurality of formation areas, and applying at least one electromagnetic field on each of the formation areas, thereby forming the tubular object at each of the formation areas.

The method can further include a step of determining the formation area on the object. The mandrel can include at least one opening, in which case, the step of placing, includes positioning of a selected one of the openings underneath a selected one of the formation areas. Hence, the step of applying the electromagnetic field causes punching of material within the selected formation area.

The tubular object can be made of shape memory material. The method can further include a preliminary step of applying shape memory characteristics to the tubular object. Alternatively, the method can further include a final step of applying shape memory characteristics to the tubular object.

According to a further aspect of the invention, the above at least one object can include a plurality of wires. Thus, the formation area is defined by an overlap intersection of at least two of the wires. For example, the method can further include a step of placing the wires in a crosswise structure.

It is noted that at least selected ones of the wires can be straight or curved. These wires can be made of any of the above list of materials, and treated accordingly, before or after formation.

In accordance with a further preferred embodiment of the present invention, there is provided a medical support device, which includes a tubular object. The tubular object includes a plurality of openings, wherein at least selected ones of the openings were electromagnetically formed. This tubular object can be is made of any of the above list of materials In accordance with a further preferred embodiment of the present invention, there is provided a medical support device, which includes a sheet of conductive material. The sheet of conductive material is folded so as to provide a tubular object, where one edge of the sheet of conductive material overlaps the other, thereby defining an overlapping section. The overlapping edges are joined by means of electromagnetic forming. This medical support device can further include a plurality of openings, where at least some of them were formed according to EMF or according to conventional forming techniques such as drilling, laser cutting, chemical etching, fluid punching, electrical discharge machining, chemical machining, photochemical blanking, abrasive material flow machining, ultrasonic machining, hydrodynamic machining, stamping, and the like.

The sheet of conductive material can be made of any of he above listed materials. The method can have a preliminary or a final step of applying shape memory characteristics to the sheet of conductive material.

In accordance with another preferred embodiment of the present invention, there is provided a medical support device, which includes a sheet of conductive material. The sheet of conductive material includes a plurality of openings, which are formed by electromagnetic forming. The sheet of conductive material is folded so as to provide a tubular object, where one edge of the sheet of conductive material overlaps the other, thereby defining an overlapping section.

The joining of the overlapping edges within the overlapping section can be made using EMF or by conventional techniques such as arc welding, gas welding, resistance welding, soldering, brazing, electron beam welding, laser beam welding, friction welding, diffusion bonding, explosive welding, adhesive bonding, and the like.

In accordance with a further preferred embodiment of the present invention, there is provided a method for producing a medical support device from a sheet of formable material. The method includes the steps of: placing a predetermined mandrel against a plurality of formation areas, and applying at least one electromagnetic field on each of the formation areas, thereby forming the sheet at each of the formation areas. The method can further include a step of determining the formation area on the object.

The mandrel can include at least one opening. In this case the step of placing includes positioning a selected one of the openings underneath a selected one of the formation areas. Hence, the step of applying the electromagnetic fields causes shearing of material within the selected formation area.

The sheet of formable material is made of any of the above materials.

The method can further include a step of folding the sheet of formable material, thereby producing a tubular object.

According to one aspect of the invention, at least selected ones of the formation areas are located in overlapping sections of the sheet of formable material, the overlapping sections being defined in the step of folding.

Depending on various considerations, which arise from the physical organ to be treated, the formable material can either be electrically conductive or not electrically conductive.

In accordance with a further preferred embodiment of the present invention, there is provided a method for producing a medical support device including the steps of: placing a plurality of wires wherein at least a section of each of the wires overlaps a section of at least another of the wires, each of the overlapping section defining an intersection area, and applying at least one electromagnetic field on the overlapping wires of each of the intersection area, thereby joining each of the wires at the intersection area.

The method can further include a step of repeating the step of applying, thereby forming a mesh like structure of the wires. The method can also include a step of folding the mesh, thereby forming a cylinder.

The wires can be generally straight or curved. The arrangement of the wires can be crosswise. At least selected ones of the wires can be made of shape memory alloy, or any of the above listed materials.

In accordance with a further preferred embodiment of the present invention, there is provided a medical support device, which includes a plurality of wires. Each of the wires intersects with at least another of the wires, thereby defining a plurality of intersection points, thereby forming a mesh, where the mesh is folded to in the shape of a cylinder. At least selected ones of the intersecting wires are joined to the wires intersecting therewith, by means of electromagnetic forming process.

BRIEF DESCRIPTION OF THE DRAWINGS CORRECT DRAWING LIST

The present invention will be understood and appreciated more fully from the following detailed description taken in conjunction with the drawings in which.

DETAILED DESCRIPTION OF PREFERRED EMBODIMENTS

The present invention overcomes the disadvantages of the prior art by providing a novel method for manufacturing medical support devices and elements, using electromagnetic forming (EMF) techniques.

Figure 1:
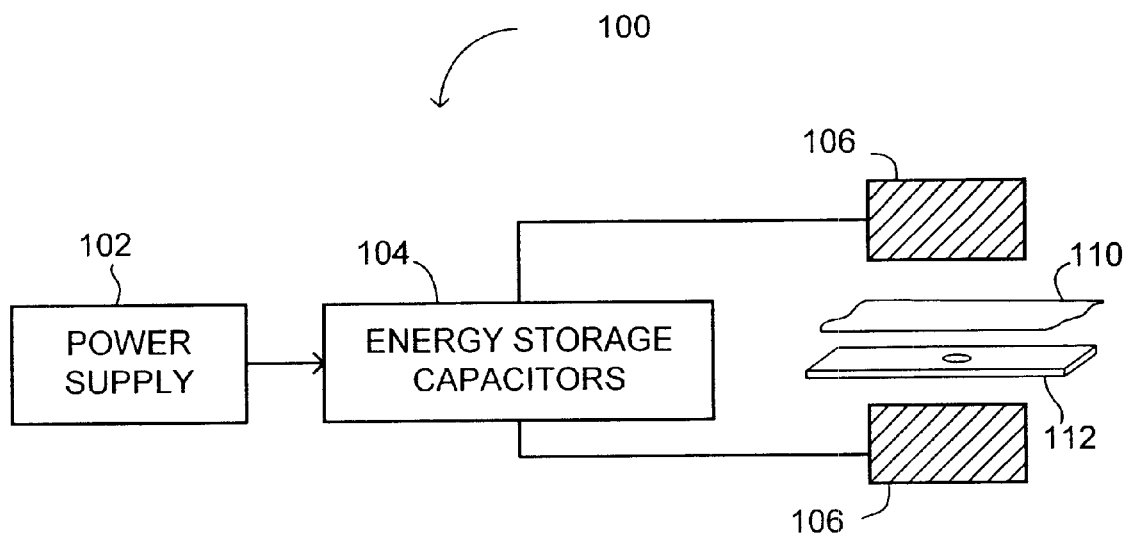
FIG. 1, is a schematic illustration of a system for manufacturing metal medical support elements, constructed and operative in accordance with a preferred embodiment of the present invention.

Reference is now made to FIG. 1, which is a schematic illustration of a system for manufacturing metal medical support elements, generally referenced 100, constructed and operative in accordance with a preferred embodiment of the present invention.

System 100 includes a forming coil 106 (electromagnetic generators), an energy storage capacitors 104 and a power supply 102. The energy storage capacitors 104 are connected to the power supply 102 and to the forming coil—the electromagnetic field generator 106. In the present example, the electromagnetic field generator includes a metal coil.

The forming coil 106 is placed around a conductive metal object, generally referenced 110 and produce pulses of electromagnetic field. A field shaper mandrel 112 is inserted between the work piece 110 and the coil 106. The electromagnetic generator (forming coil 106) produces pulses of electromagnetic field. This very intense electromagnetic field is produced by the discharge of a bank of capacitors 104 into the forming coil 106. The resulting eddy currents that are induced in the conductive metal object, then interact with the magnetic field to cause mutual repulsion between the conductive metal work-piece 110 and the forming coil 106. The force of this repulsion is sufficient to stress the metal work-piece beyond its yield strength, resulting in a permanent deformation. The field shaper mandrel 112 is used to concentrate the magnetic field at the points at which the forming/cutting is desired. The magnetic pressure is localized in certain regions of the metal work-piece. This technique most efficiently uses stored energy to produce high local forming pressures in desired areas. In the present example, mandrel 112 includes a hole. Accordingly, the apparatus 100 can Electro-Magnetically "punch" a hole in the work-piece, by accelerating the metal work piece in the vicinity of the hole, towards it.

Figure 2:
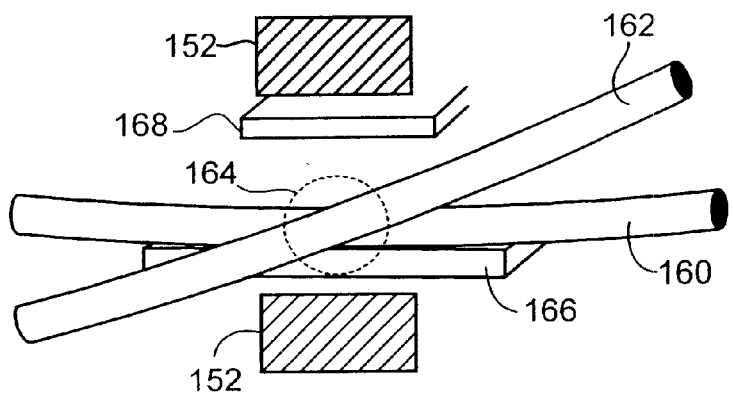
FIG. 2, is an illustration of two wires to be joined together and a forming coil, constructed and operative in accordance with another preferred embodiment of the invention.

Reference is now made to FIG. 2, which is an illustration of two wires to be joined together and a forming coil, constructed and operative in accordance with another preferred embodiment of the invention. Wires 162 and 160 are placed one over the other, whereby they cross each other at a crossing section 164. A support member 166 is placed underneath wire 160. An accelerator element 168 can be placed over the crossing section 164. Forming coil 152 is located around the crossing section 164 and the supporting member 166. At a predetermined moment, the forming coil 152 produces a magnetic field pulse. This electromagnetic field accelerates the two wires, towards the support member 166, thereby forcing them to join at the crossing section 164. At the same time, the magnetic field pulse also accelerates the accelerator element 168 towards the support member 166. Accelerator element 168 can be used in various cases where additional forces are required, such as, when the two joined pieces are characterized by poor conductivity or non at all.

It is noted that the material characteristics of the two wires 162 and 160 are not changed outside the crossing section 164. The strength of the welded joint is at least comparable to the strength of the parent material.

Figure 3A:
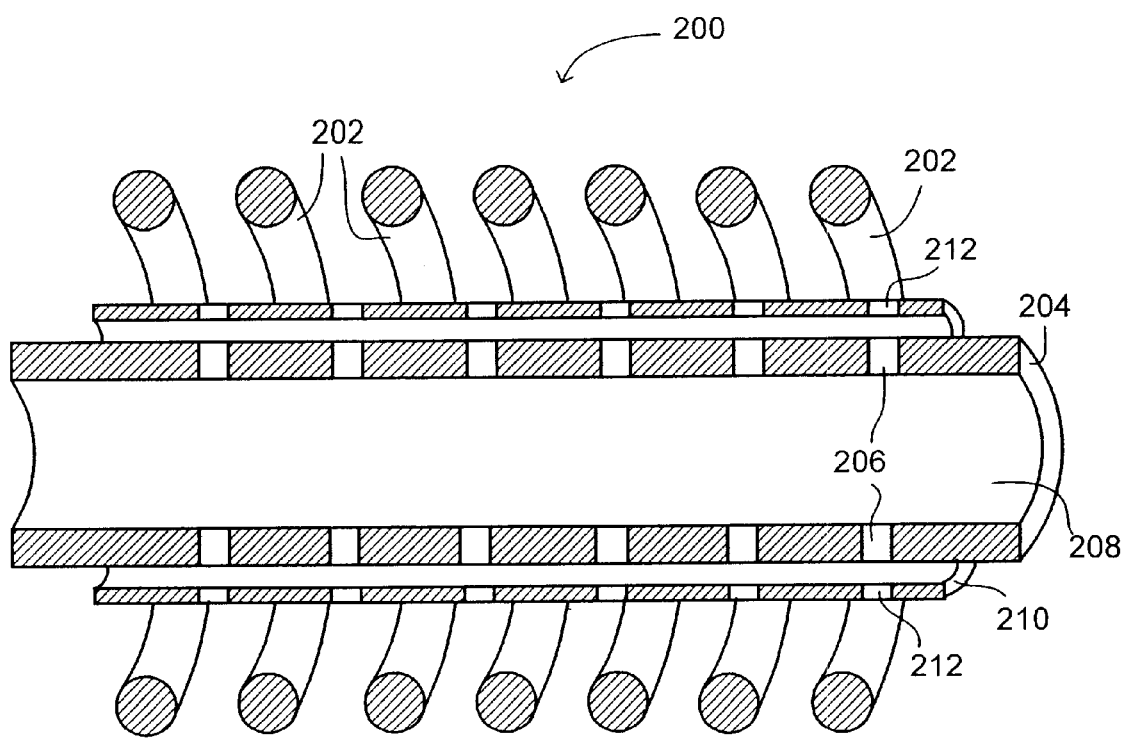
FIG. 3A, is a cross sectional illustration of a stent manufacturing device, constructed and operative in accordance with yet another preferred embodiment of the present invention.

Reference is now made to FIG. 3A, which is a cross sectional illustration of a stent manufacturing device, generally referenced 200, constructed and operative in accordance with another preferred embodiment of the present invention. Device 200 includes a mandrel 204 and a coil 202. Mandrel 204 is a general hollow tube (defined by a shaft 208), which includes a plurality of holes 206, at the perimeter thereof. Mandrel 204 is concentrically placed within coil 202. A tubular work-piece 210 is concentrically placed between mandrel 204 and coil 202.

Figure 3B:
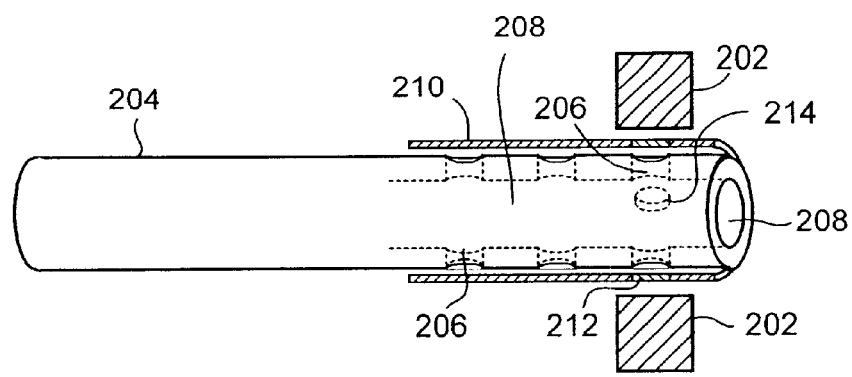
FIG. 3B, is a cross sectional view of the stent manufacturing device and the work-piece of FIG. 3A, constructed and operative in accordance with a further preferred embodiment of the present invention.

Reference is further made to FIG. 3B, which is a cross sectional view of device 200 and work-piece 210 of FIG. 3A. Coil 202 produces an electromagnetic pulse, when an electrical current pulse is conducted there through. This magnetic pulse causes a counter flow of electrical current within the work-piece 210. The vector combination of the electromagnetic field and the counter electric current, causes the generation of mechanical forces on the work-piece 210, which are directed towards the center of mandrel 204.

As a result, pieces (generally referenced 214) of material of the work-piece 210 are sheared against openings 206, thus producing holes 212. In accordance with one aspect of the present invention, the various portions of the work-piece 210 can be punched in a single cycle. Alternatively, the entire work-piece 210 can be punched in a single cycle. It is noted that the material characteristics of the work-piece 210 are substantially maintained throughout and after the punching process. The amount of heat, generated through the process of the present invention is significantly reduced with comparison to other method for manufacturing stents from a single work-piece.

Figure 4A:
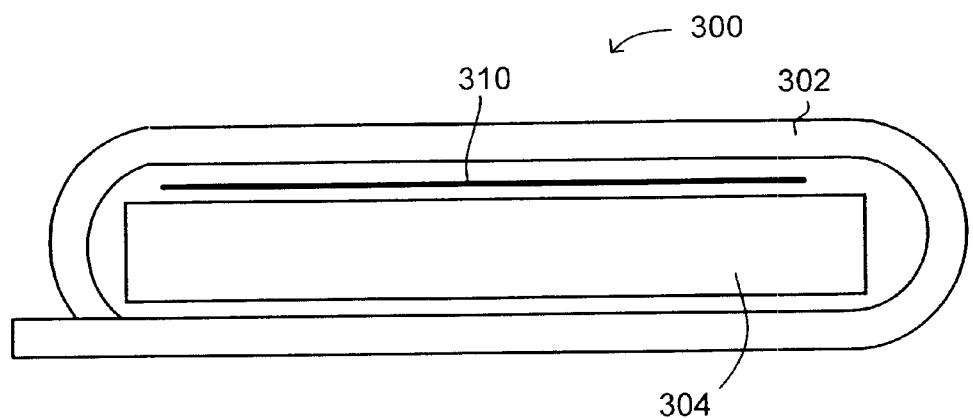
FIG. 4A is a side view illustration of a work-piece, constructed and operative in accordance with another preferred embodiment of the present invention.
Figure 4B:
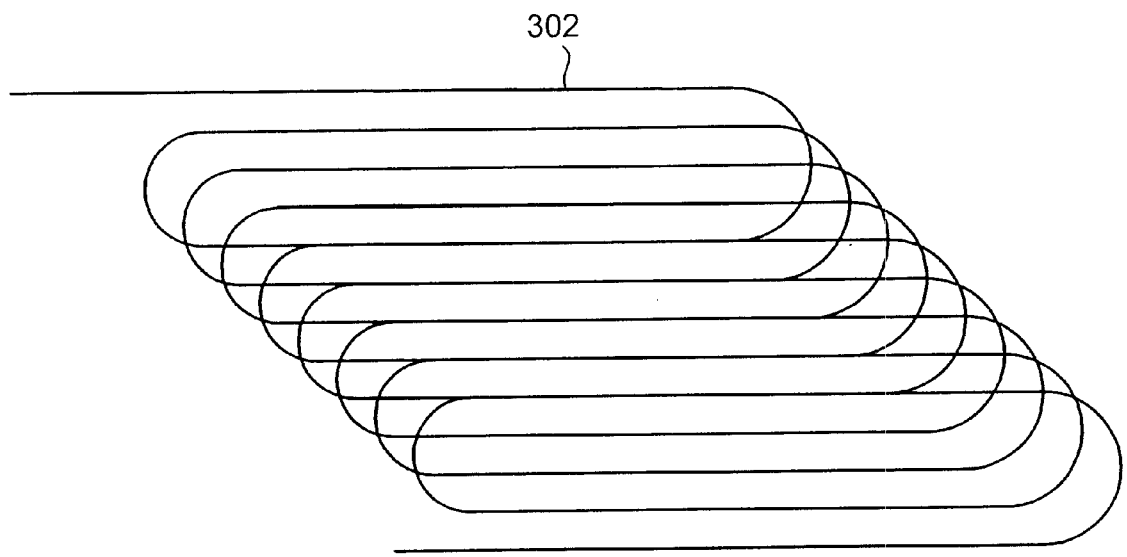
FIG. 4B is an illustration in perspective of the coil of the device of FIG. 4A, constructed and operative in accordance with a further preferred embodiment of the present invention.
Figure 4C:
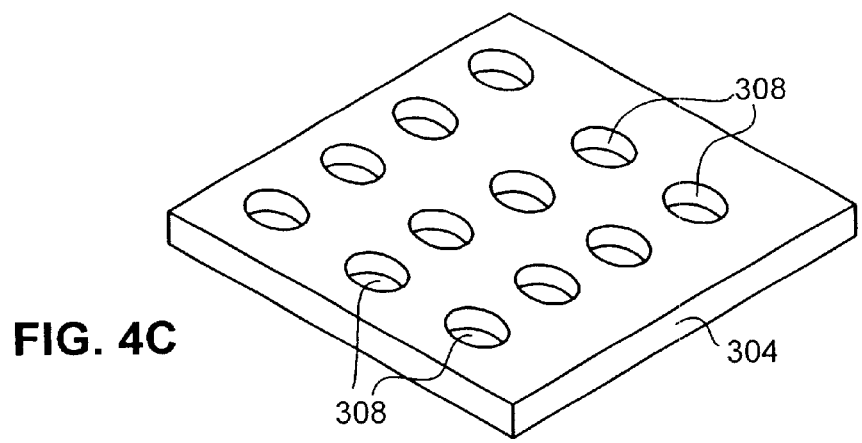
FIG. 4C is an illustration in perspective of the mandrel of the device of FIG. 4A, constructed and operative in accordance with a further preferred embodiment of the present invention.
Figure 4D:
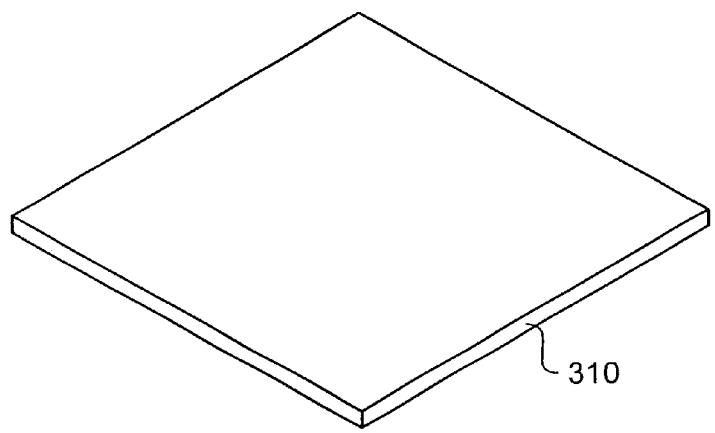
FIG. 4D is an illustration in perspective of the work-piece of FIG. 4A, constructed and operative in accordance with another preferred embodiment of the present invention.

Reference is now made to FIGS. 4A, 4B, 4C and 4D. FIG. 4A is a side view illustration of a work-piece, generally referenced 310, and a device, generally referenced 300, for executing a preliminary stage in the manufacturing of a tubular device, constructed and operative in accordance with another preferred embodiment of the present invention. FIG. 4B is an illustration in perspective of the coil of the device of FIG. 4A. FIG. 4C is an illustration in perspective of the mandrel of the device of FIG. 4A. FIG. 4D is an illustration in perspective of the work-piece of FIG. 4A.

Device 300 includes a coil 302 and a mandrel 304. Coil 302 is a flat coil, which is adapted to surround flat objects (FIG. 4B). Mandrel 304 (FIG. 4C) is a flat surface, which includes a plurality of holes, generally referenced 308. Mandrel 304 is placed within coil 302 (FIG. 4A). Work-piece 310 is placed within coil 302, adjacent to mandrel 304. When coil 302 conducts a strong electric pulse, it produces a respective magnetic field pulse, therein. The magnetic field induces electrical current in the work-piece 310, and in turn causes mechanical forces which drive the work-piece 310 towards mandrel 304. These forces are significantly strong and press the work-piece 310 against mandrel 304. In the present example, these forces cause shearing of work-piece material, where the mandrel 304 exhibits a sharp edge, such as in holes 308.

Figure 4E:
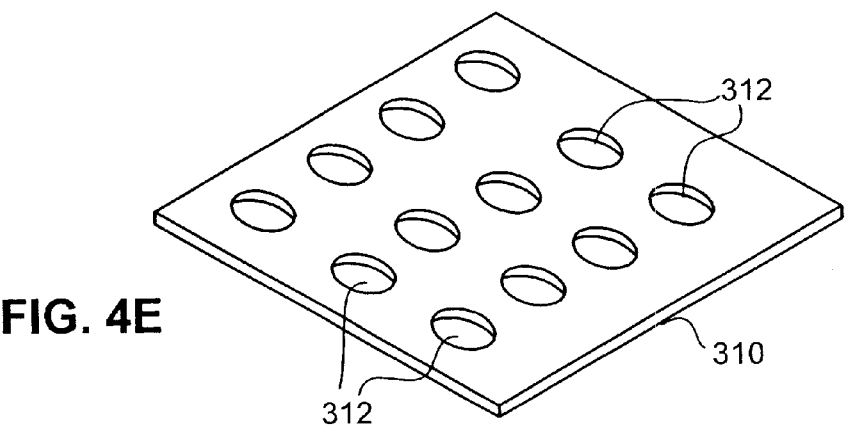
FIG. 4E is an illustration in perspective of work-piece, after being treated by the device of FIG. 4A.

Reference is further made to FIG. 4E, which is an illustration in perspective of work-piece 310, after being treated by device 300. Now, work-piece 310 includes holes, generally referenced 312, in a pattern, which is respective of the hole pattern of mandrel 304. The above device and procedure, provide means for perforating a pattern of holes in a material sheet, which can be further folded, and formed to a shape of a perforated tube. The edges of the material sheet may joined by metal joining methods known in the art, such as arc welding, gas welding, resistance welding, soldering, brazing, electron beam welding, laser beam welding, friction welding, diffusion bonding, explosive welding, ultrasonic welding, adhesive bonding, EMF forming, and the like.

Figure 5:
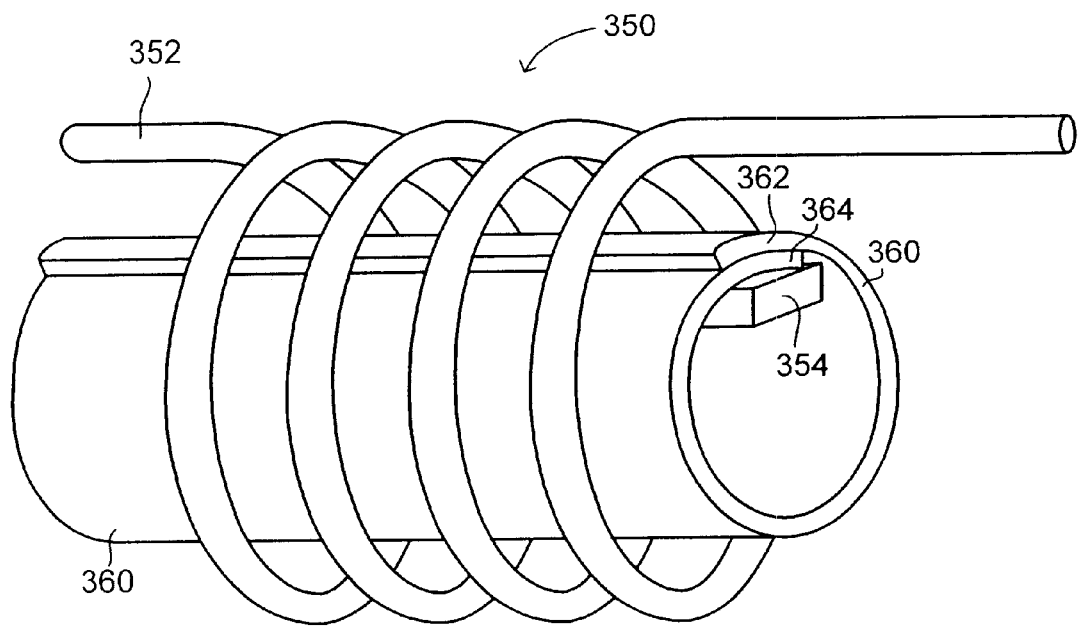
FIG. 5, is an illustration in perspective of a forming device, constructed and operative in accordance with another preferred embodiment of the present invention.

Reference is now made to FIG. 5, which is an illustration in perspective of a forming device, generally referenced 350, constructed and operative in accordance with another preferred embodiment of the present invention. Device 350 includes a coil 352 and a mandrel 354. Mandrel 354 is massive support device, which is fixed to its place. A work-piece 360 is made of a generally flat sheet of material, which is folded to form a tubular object. Device 350 is designed to firmly connect the overlapping edges 362 and 364 of work-piece 360, thereby producing a closed shape. Work-piece 360 is inserted in coil 352. Mandrel 354 is inserted inside work-piece 360, and placed in the vicinity of overlapping edges 362 and 364. As a strong pulse of electric current flows through the wire, which comprises coil 352, the coil 352 produces a strong magnetic field pulse. This magnetic pulse, causes a counter electric current pulse in work-piece 360. The vector combination of the magnetic pulse and the counter electric current pulse, produce a mechanical force, which accelerates overlapping edges 362 and 364 towards mandrel 354. The strong impact force, causes the two overlapping edges 362 and 364 to join together, thereby producing a closed, cylinder. It is noted that this procedure can be performed on work-pieces, which were treated according to the procedure presented above, in conjunction with FIG. 4A. Alternatively, this procedure can be used independently, for work-pieces, which were initially treated by any other forming technique known in the art. Such techniques include laser beam machining, electrical discharge machining, electrochemical machining, chemical machining, photochemical blanking, abrasive jet machining, abrasive flow machining, ultrasonic machining, hydrodynamic machining, electronic beam machining, stamping, fine blanking, drilling, and the like.

It is noted that the present invention can also be implemented for forming materials, which exhibit poor electric conductivity or non at all, by utilizing an accelerator element. The accelerator element is made of highly electrical conductive material, which provides high-induced currents.

Figure 6:
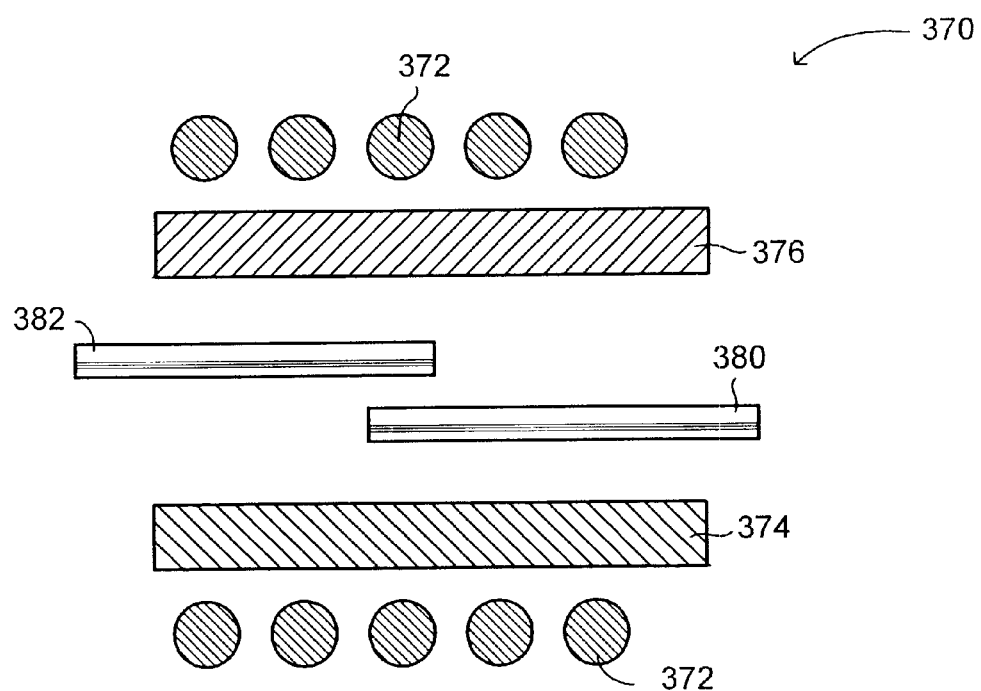
FIG. 6, is a cross-sectional illustration of a forming device, constructed and operative in accordance with a further preferred embodiment of the present invention.

Reference is now made to FIG. 6, which is a cross-sectional illustration of a forming device, generally referenced 370, constructed and operative in accordance with a further preferred embodiment of the present invention. Device 370 includes a coil 372, a mandrel 374 and an accelerating element 376. Two work-pieces 380 and 382 are inserted in coil 372, overlapping each other.

Figure 7A:
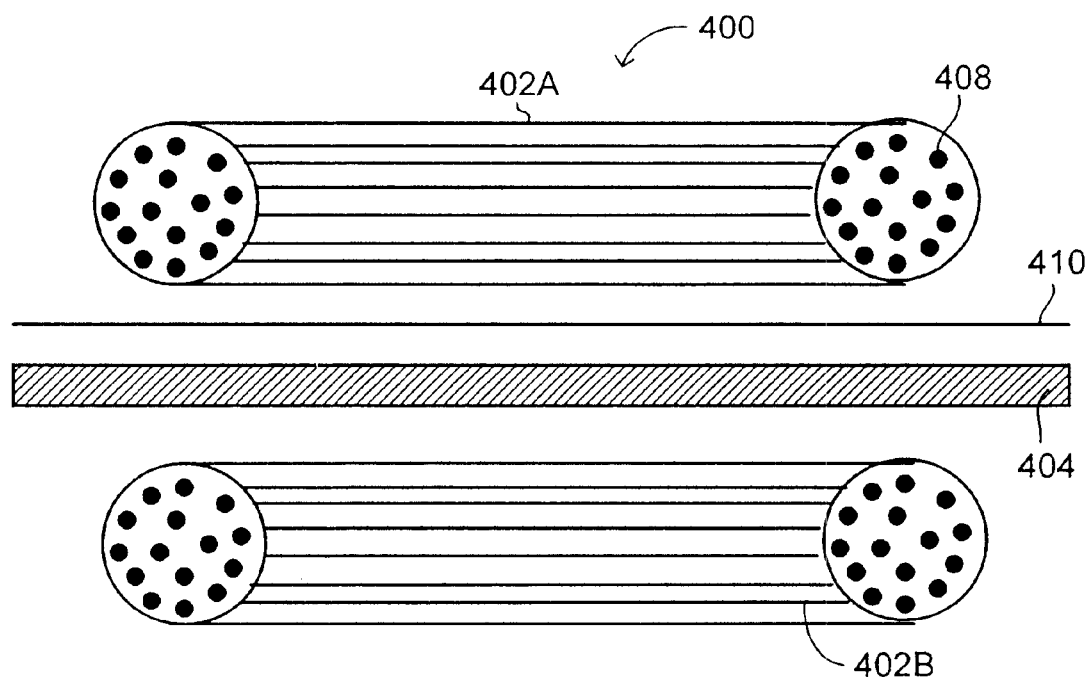
FIG. 7A is a cross-sectional illustration of a forming device, constructed and operative in accordance with another preferred embodiment of the present invention.
Figure 7B:
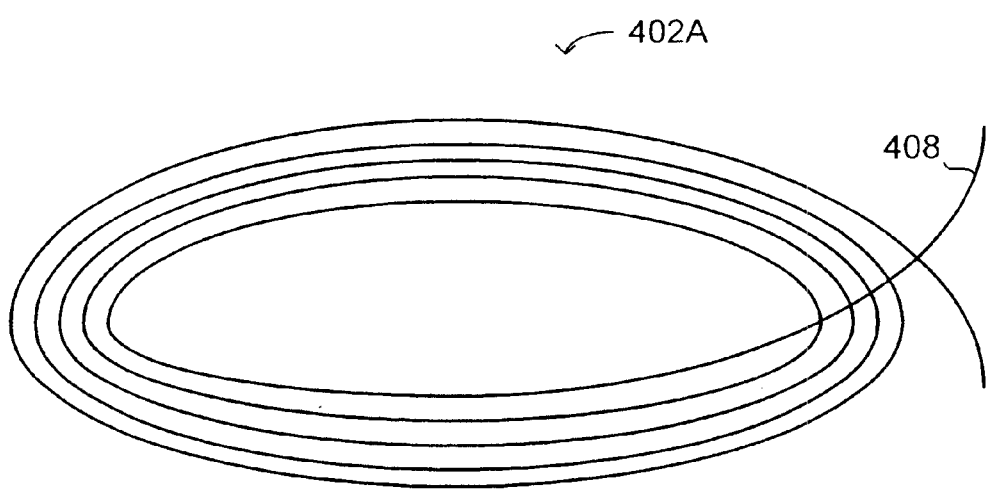
FIG. 7B is an illustration in perspective of a coil of the device of FIG. 7A, constructed and operative in accordance with a further preferred embodiment of the present invention.

Reference is now made to FIGS. 7A and 7B. FIG. 7A is a cross-sectional illustration of a forming device, generally referenced 400, constructed and operative in accordance with another preferred embodiment of the present invention. FIG. 7B is an illustration in perspective of a coil of the device of FIG. 7A. Device 400 includes a pair of coils 402A and 402B and a mandrel 404. Coils 402A and 402B each is designed and constructed in the form of a ring.

The coils 402A and 402B are positioned parallel to each other. Mandrel 404 is placed between the coils 402A and 402B. A work-piece 410 is placed between coil 402A and mandrel 404, in close vicinity to coil 402A. When wire 408 conducts an electric current pulse, it produces in turn, a magnetic field pulse, which is induced onto work-piece 410. Work-piece 410 produces a counter electric current. The vector combination of the magnetic field and the counter electric current pulse produces a mechanical force, which accelerates work-piece 410 towards mandrel 404. Work-piece 410 is deformed depending on the shape (curves and openings) which characterizes mandrel 404.

Figure 7C:
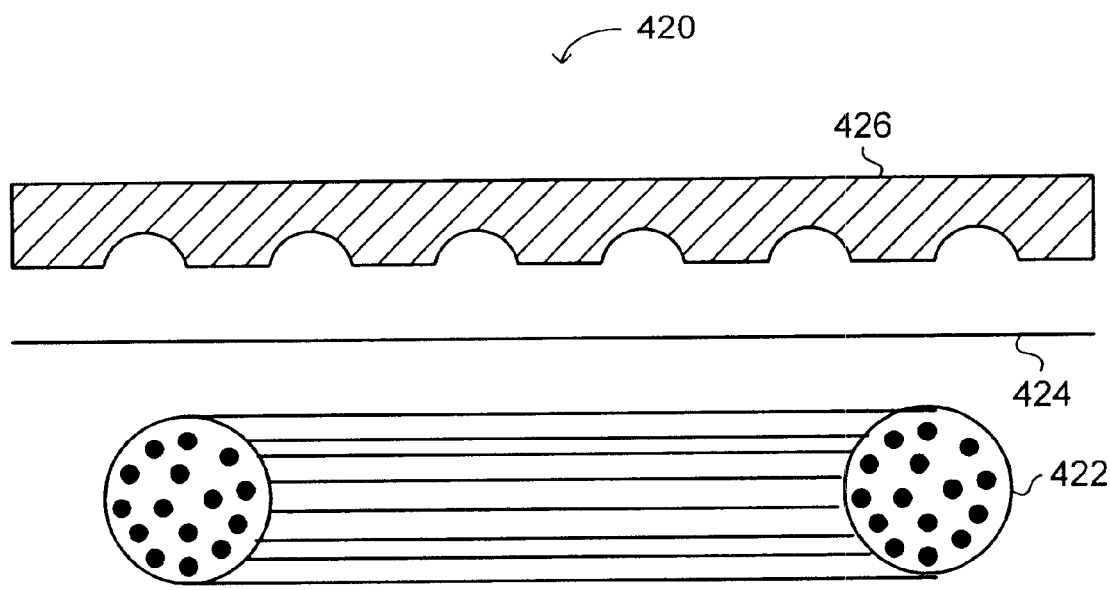
FIG. 7C, is a-cross-sectional illustration of a forming device, constructed and operative in accordance with a further preferred embodiment of the present invention.

Reference is further made to FIG. 7C, which is a cross-sectional illustration of a forming device, generally referenced 420, constructed and operative in accordance with a further preferred embodiment of the present invention. The forming device includes a coil 422 similar to coil 402A as described with reference to FIG. 7A, and a mandrel 426. A work-piece 424 is placed between the coil 422 and mandrel 426. Work-piece 424 is deformed depending on the shape (curves and openings) which characterizes mandrel 426, in a process similar to that described with respect to FIG. 7A.

Figure 8:
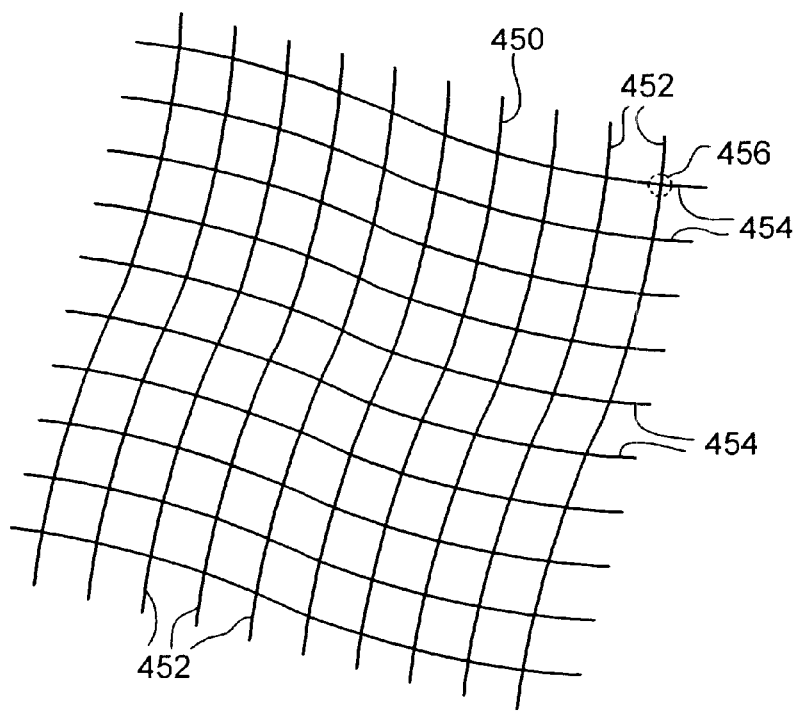
FIG. 8, is a schematic illustration of a metal web, constructed in accordance with another preferred embodiment of the present invention.

Reference is now made to FIG. 8, which is a schematic illustration of a metal web, generally referenced 450, constructed in accordance with another preferred embodiment of the present invention.

Web 450 is formed of a plurality of wires, generally referenced 452 and 454. These wires are arranged in a crosswise structure, wherein the length portion is comprised by wires 452, and the breadth portion is comprised by wires 454. An intersection between a selected length wire 452 and a selected breadth wire 454 is denoted 456. In the present example, the upper right intersection 456 is further denoted by a circle. In accordance with the present invention, each of these intersections, is joined using electromagnetic forming techniques.

It is noted that each of the wires 452 and 454 can be made using a different metal or conductive compound material.

For example, the length portion wires can be made of elastic alloys while the breadth portion wires are made of shape memory alloys. It is noted that the use of electromagnetic forming, simplifies the manufacturing process, while maintaining the original characteristics of the materials used, such as elasticity, plasticity, shape memory characteristics and the like.

Figure 9A:
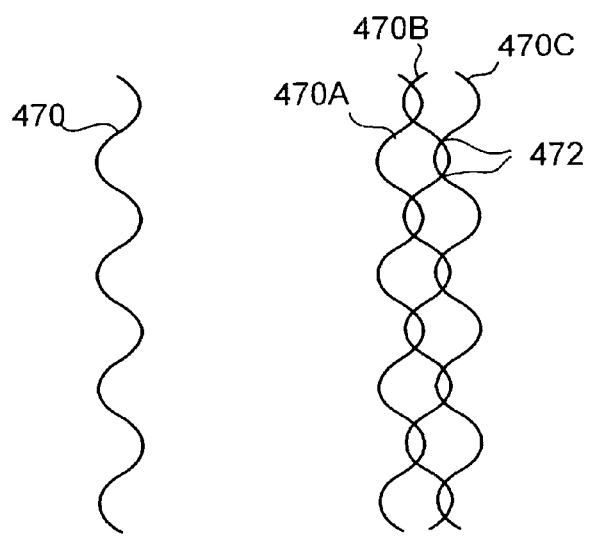
FIG. 9A, is a schematic illustration of a plurality of wire elements, and a wire structure, constructed and operative in accordance with a further preferred embodiment of the invention.

Reference is now made to FIG. 9A, which is a schematic illustration of a plurality of wire elements, generally referenced 470, and a wire structure, constructed and operative in accordance with a further preferred embodiment of the invention.

Wire 470 is shaped, generally as a uniform sinus waveform. Wires 470A, 470B and 470C, being identical to wire 470, form a mesh structure, when placed side by side and joined at selected intersections (generally referenced 472) thereof, by means of electromagnetic forming techniques.

It is noted that similarly to the structure of FIG. 8, various types of material can be used to form each of the wires 470. Hence, the structure can be made of many different materials. In the present example, wire 470A is made of shape memory material having a two-way action, at two different temperatures, wire 470B is made of shape memory alloy having a one way action, at a predetermined temperature and wire 470C is made of a spring alloy. It is noted that alloys having plastic characteristics can also be used for such wires.

Figure 9C:
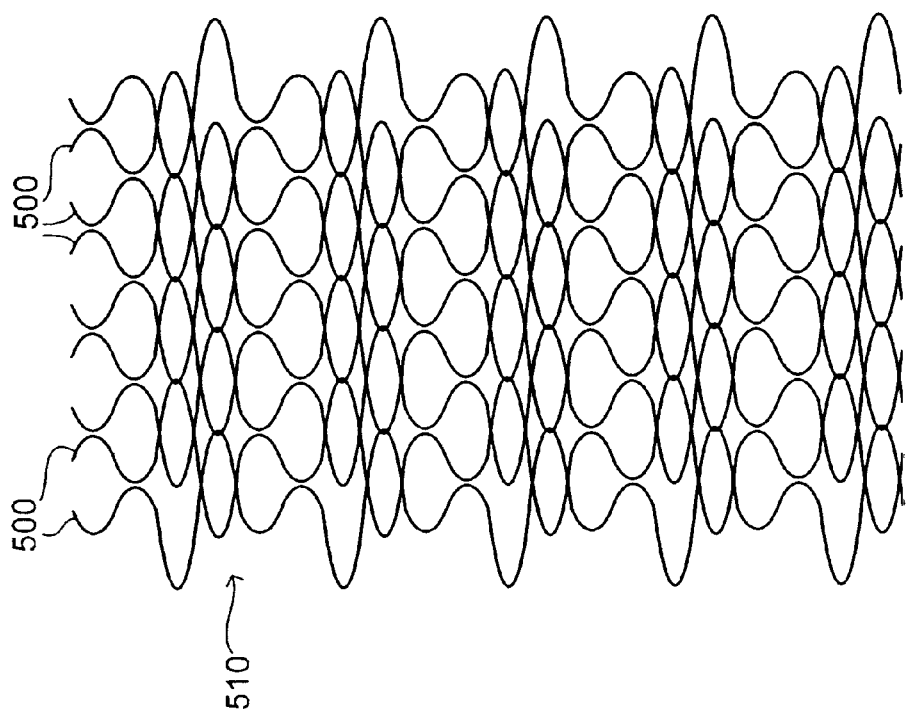
FIG. 9C is an illustration of a mesh structure, constructed in accordance with a further preferred embodiment of the present invention.
Figure 9B:
FIG. 9B is an illustration of a wire, constructed in accordance with another preferred embodiment of the present invention.

Reference is now made to FIGS. 9B and 9C. FIG. 9B is an illustration of a wire, generally referenced 500, constructed in accordance with another preferred embodiment of the present invention. FIG. 9C is an illustration of a mesh structure, generally referenced 510, constructed in accordance with a further preferred embodiment of the present invention.

Wire 500 is shaped as a non-uniform wave function, having "maximum" locations, generally referenced 502 and 504. It is noted that in accordance with further aspects of the invention, this wave function can include a combination of any known wave function, such as triangles, square, chain-saw and the like. With reference to FIG. 9C, a plurality of wires 500 are joined together by means of electromagnetic technique, to form mesh structure 510.

Figure 9D:
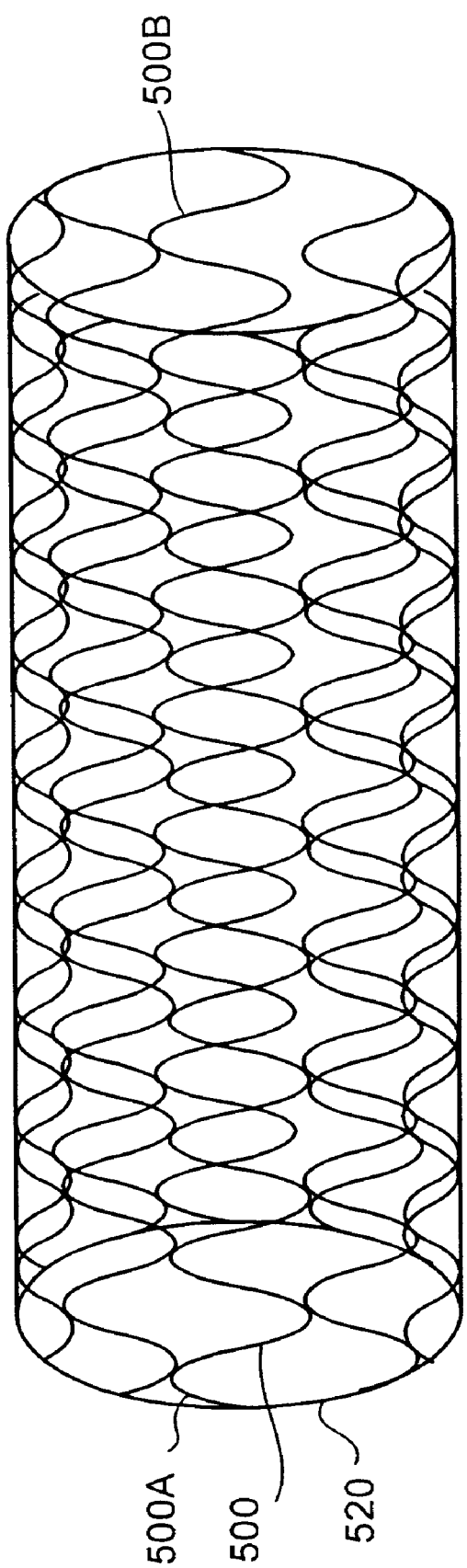
FIG. 9D, is an illustration of a medical support device, constructed and operative in accordance with another preferred embodiment of the invention.

Reference is further made to FIG. 9D, which is an illustration of a medical support device, generally referenced 520, constructed and operative in accordance with another preferred embodiment of the invention. In general, each of the mesh or web structures presented above, can be used to form a medical support device such as a stent or a catheter tip. In the present example, mesh 510 is curved so that the left side meets the right side thereof, thereby forming the cylinder, which comprises support device 520. It is noted that the intersections between the left side wire 500A and the right side wire 500B can be fixed together by means of electromagnetic forming techniques, where one electromagnetic coil is placed around the tube mesh, or by any other joining technique like laser welding.

Figure 10A:
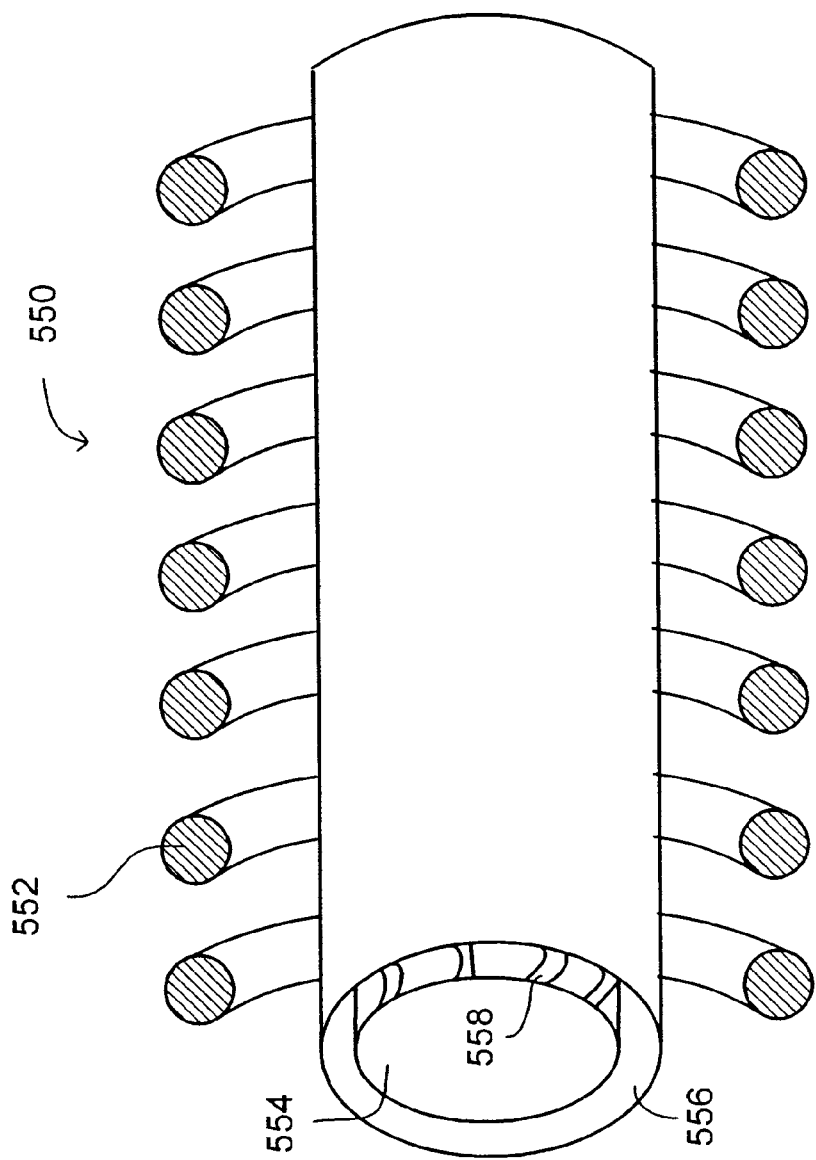
FIG. 10A is an illustration in perspective of a forming device, constructed and operative in accordance with a further preferred embodiment of the present invention.
Figure 10B:
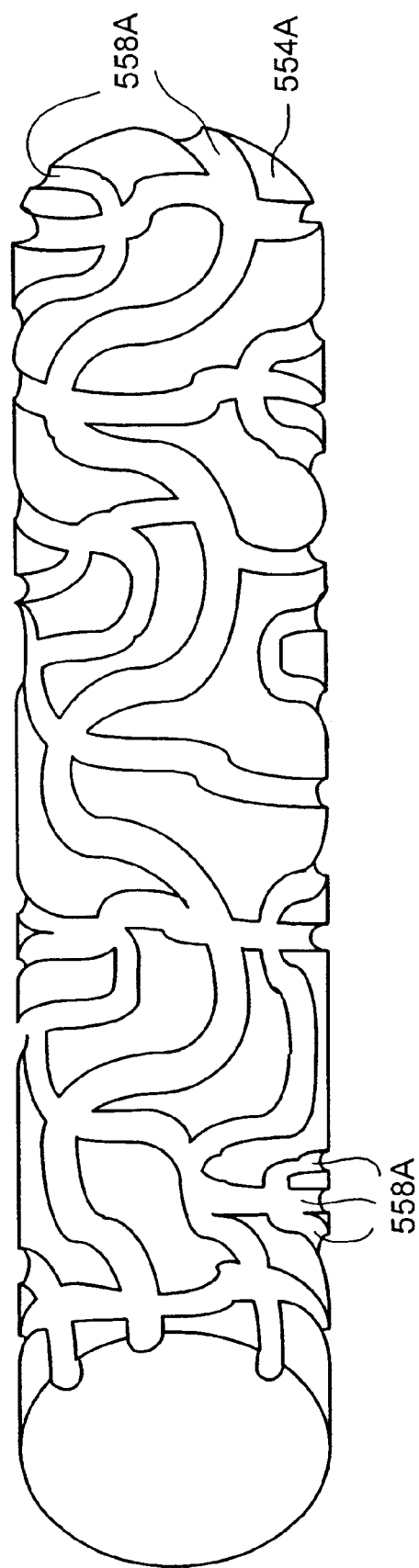
FIG. 10B is an illustration in perspective of a mandrel, for use with the forming device of FIG. 10A, constructed and operative in accordance with another preferred embodiment of the present invention.
Figure 10C:
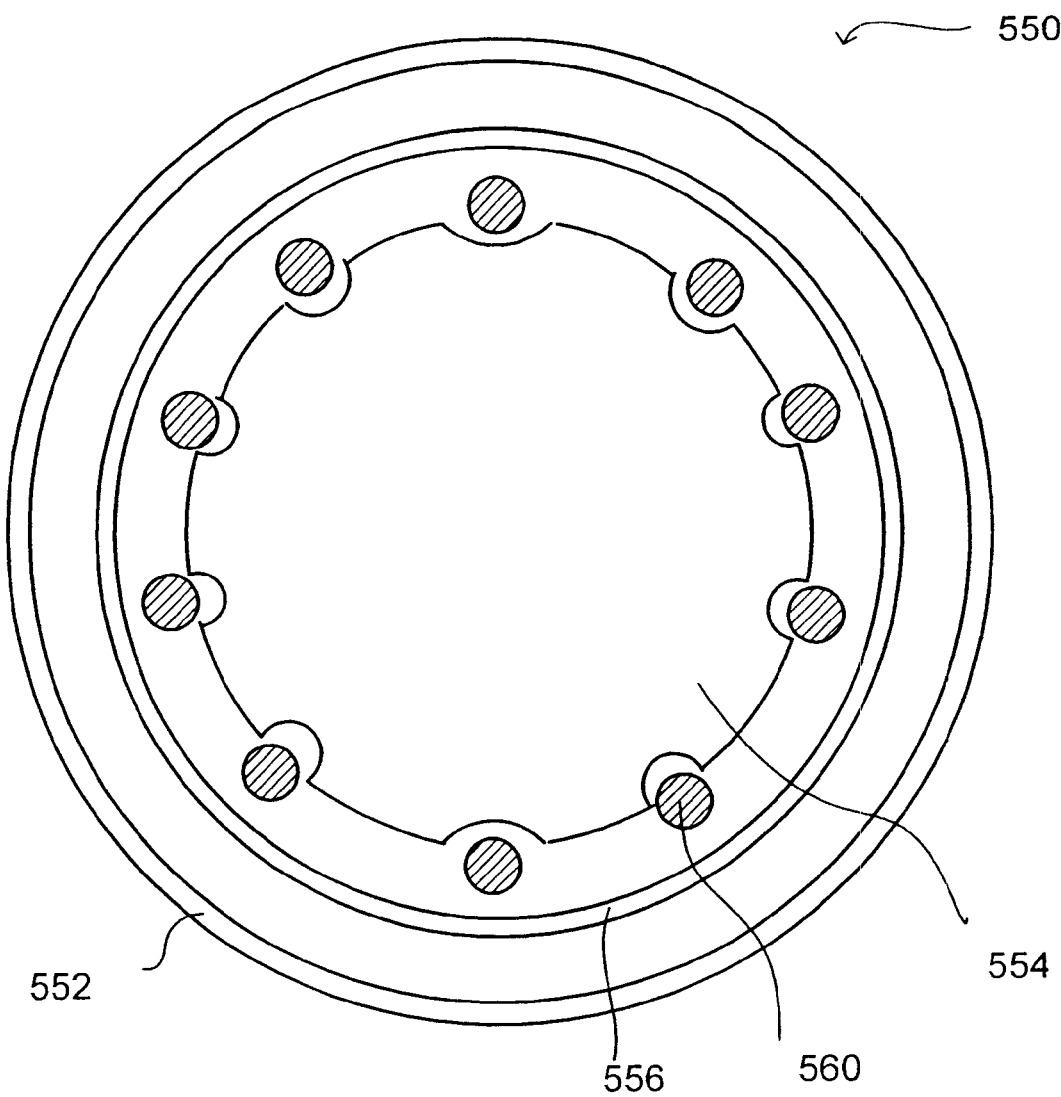
FIG. 10C is a side view of forming device of FIG. 10A, constructed and operative in accordance with a further preferred embodiment of the present invention.

Reference is now made to FIGS. 10A, 10B, and 10C. FIG. 10A is an illustration in perspective of a forming device, generally referenced 550, constructed and operative in accordance with a further preferred embodiment of the present invention. FIG. 10B is an illustration in perspective of a mandrel, generally referenced 554A, for use with the forming device 550 of FIG. 10A, constructed in accordance with another preferred embodiment of the present invention. FIG. 10C is, a side view of forming device 550 of FIG. 10A.

Forming device 550 includes a forming coil 552 and a mandrel 554 and a conductive layer 556. Mandrel 554 is adapted to receive a plurality of wires, arrange them in a predetermined structure and hold them together during the forming procedure. With reference to FIG. 10B, mandrel 554A includes a plurality of groves, generally referenced 558A, which define a web like structure. These grooves are then filled with wires and formed within device 550.

Referring both to FIGS. 10A and 10C, a plurality of wires, generally referenced 560 are placed in the grooves 558. Mandrel 554 and the inserted wires 560 are wrapped with conductive layer 556, which increases the conductivity of the wire structure. Similar to devices presented herein above, the coil 552 produces a magnetic field pulse as an electric current pulse flows there through. In turn, the combination of conductive layer 556 and wires 560 produce a counter electric current and the combination of the above produces a mechanical force, which bonds the wires together.

It will be appreciated by persons skilled in the art that the present invention is not limited to what has been particularly shown and described here in above. Rather the scope of the present invention is defined only by the claims which follow.

What is claimed is:

1. A method for producing a medical support device capable of insertion into the body, the method comprising the steps of:

positioning an object having an original physical configuration in the vicinity of an electromagnetic field generator and substantially proximate a forming mandrel, said forming mandrel having a mandrel physical configuration;

inducing electromagnetic forces in said object which accelerate said object toward said forming mandrel; and changing said original physical configuration to a second physical configuration, said second physical configuration being influenced by said mandrel's physical configuration.

2. A method for producing a medical support device capable of insertion into the body, the method comprising the steps of:

positioning an object having an original physical configuration in the vicinity of an electromagnetic field generator and substantially proximate a forming mandrel, said forming mandrel having a mandrel physical configuration;

inducing electromagnetic forces in said object which accelerate the said object towards the said forming mandrel; and changing the said original physical configuration to a second physical configuration, said second physical configuration being influenced by said mandrels physical configuration.

3. The method according to claim 1, further comprising the procedure of determining a formation area of said object in the vicinity of said electromagnetic field generator.

4. The method according to claim 2, further comprising the procedure of repeating from said step of determining, so that additional formation areas define a final shape for said object, said final shape being generally cylindrical.

5. The method according to claim 3, wherein said forming mandrel includes at least one opening, and wherein said procedure of determining includes positioning a selected on of said at least one opening underneath a selected one of said formation areas, thereby causing punching of material within said selected formation area, as a result of said procedure of inducing.

6. The method according to claim 1, wherein said object comprises a tubular object.

7. The method according to claim 5, wherein said tubular object is made of a material, selected from the list consisting of:

shape memory materials;
   super elastic materials;
   stainless steel; alloys;
   polymeric materials; and
   biocompatible materials.

8. The method according to claim 1, further comprising a preliminary procedure of applying shape memory characteristics to said object.

9. The method according to claim 1, further comprising a final procedure of applying shape memory characteristics to said object.

* * * * *